Figure 1:
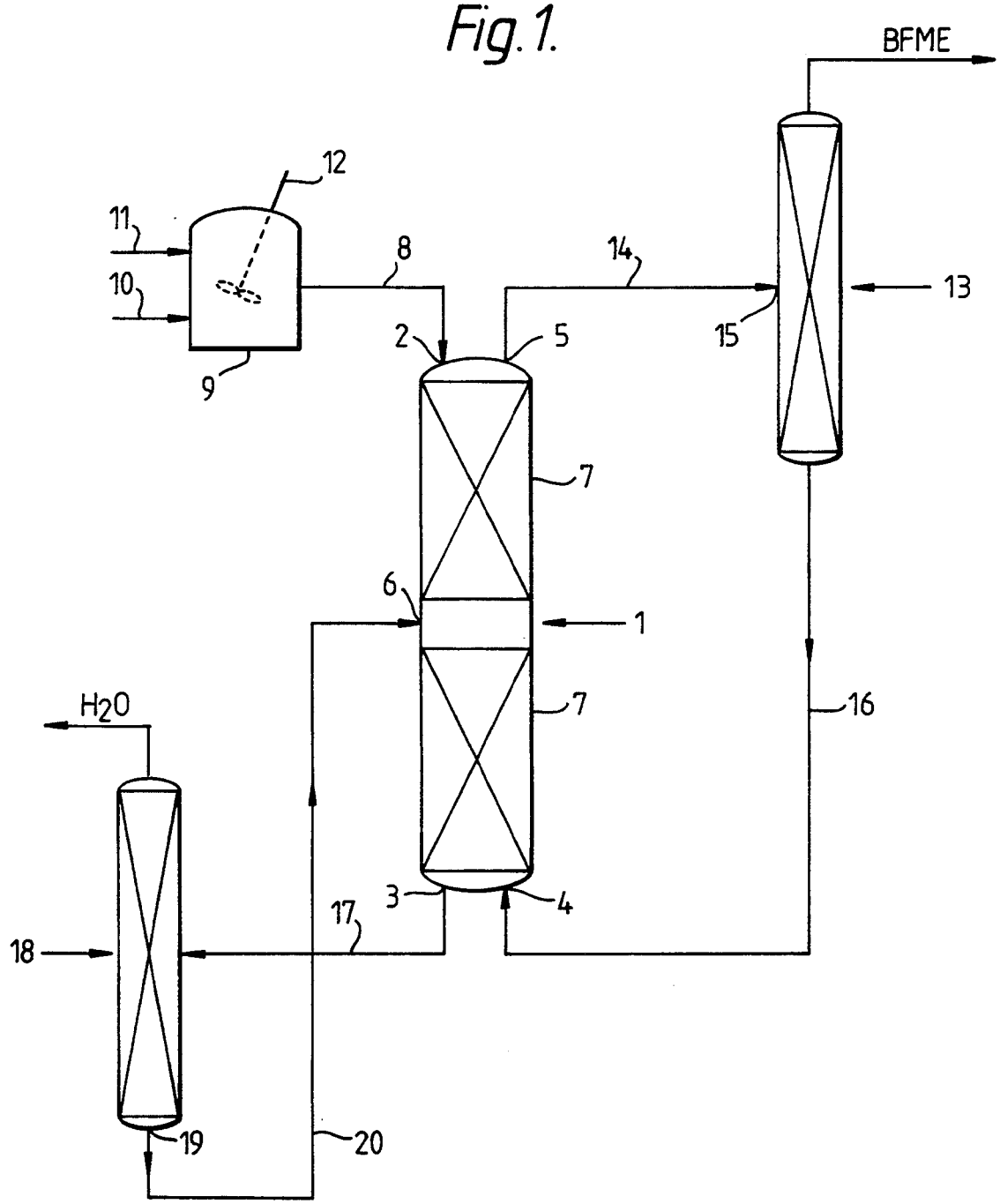

United States Patent [19]
Woodcock et al.

[11] Patent Number: 5,386,064
[45] Date of Patent: Jan. 31, 1995

[54] PRODUCTION OF BIS(FLUOROMETHYL) ETHER AND DIFLUOROMETHANE

[75] Inventors: Duncan C. Woodcock, Frodsham; Brian T. Grady, Widnes, both of Great Britain

[73] Assignee: Imperial Chemical Industries PLC, London, England

[21] Appl. No.: 47,494

[22] Filed: Apr. 19, 1993

[30] Foreign Application Priority Data

Apr. 23, 1992 [GB] United Kingdom ............ 9208769

[51] Int. Cl.$^6$ ............ C07L 41/01; C07L 17/33
[52] U.S. Cl. ............ 568/683; 570/142
[58] Field of Search ............ 568/683; 570/142

[56] References Cited
FOREIGN PATENT DOCUMENTS
518506 12/1992 European Pat. Off. .

OTHER PUBLICATIONS

Viktor Weinmayer, Hydrogen Fluoride as a Condensing Agent. VI. Reactions of Fluoroolefins with Formaldehyde in Hydrogen Fluoride, Journal of Organic Chemistry, vol. 28, No. 2, Feb. 1963, pp. 492–494.

*Primary Examiner*—Howard T. Mars
*Attorney, Agent, or Firm*—Cushman, Darby & Cushman

[57] ABSTRACT

A process for the production of bis(fluoromethyl)ether which comprises contacting formaldehyde with hydrogen fluoride in the presence of an essentially water-immiscible solvent for the ether. The bis(fluoromethyl)ether may be converted to difluoromethane, optionally after separation from the solvent, preferably by heating the bis(fluoromethyl)ether to elevated temperature in the presence of a metal, metal oxide, metal fluoride or metal oxyfluoride catalyst.

15 Claims, 2 Drawing Sheets

PRODUCTION OF BIS(FLUOROMETHYL) ETHER AND DIFLUOROMETHANE

This invention relates to a process for the production of bis(fluoromethyl)ether by the reaction of formaldehyde with hydrogen fluoride and to a process for the production of difluoromethane incorporating the step of producing bis(fluoromethyl)ether from formaldehyde and hydrogen fluoride.

Formaldehyde and hydrogen fluoride react together to produce equimolar amounts of bis(fluoromethyl)ether and water. The reaction is equilibrium limited, there being at best about a 55% conversion of formaldehyde to bis(fluoromethyl)ether at 20° C. even when using a 7:1 molar excess of hydrogen fluoride to formaldehyde to drive the equilibrium towards the products. We have discovered that in order to overcome this equilibrium problem, one or both of the products may be removed from the reaction mixture as soon as possible after it/they are formed in order that the equilibrium may be driven towards the products.

Bis(fluoromethyl)ether is useful as a starting material for the production of difluoromethane and methyl fluoride, for example by heating bis(fluoromethyl)ether to elevated temperature in the presence of a suitable catalyst. We have found that it is desirable that water is not present in significant amounts in the bis(fluoromethyl)ether which is heated since we have found that water promotes undesirable side reactions. Consequently it is desirable that water be removed from the water and bis(fluoromethyl)ether reaction product mixture before the bis(fluoromethyl)ether is further treated to produce difluoromethane and methyl fluoride.

We have now found that the aforementioned separation of bis(fluoromethyl)ether from water and separation of bis(fluoromethyl)ether product from the reaction mixture in which it is formed may be achieved efficiently using a "reactive extraction" process.

According to the present invention there is provided a process for the production of bis(fluoromethyl)ether which comprises contacting formaldehyde with hydrogen fluoride in the presence of an essentially water-immiscible solvent for the ether. The resulting solvent phase comprises more than an equimolar amount of bis(fluoromethyl)ether relative to water; this phase may then be separated from the aqueous phase. Preferably the solvent phase comprises at least twice as many moles, more preferably five times and especially ten times as many moles, of bis(fluoromethyl)ether as water.

By "reactive extraction" there is meant a process in which a product of an equilibrium reaction is extracted into a solvent phase thereby effectively removing that product from the reaction and thus driving the equilibrium towards the products. In the case of the reactive extraction process of the present invention, formaldehyde reacts with hydrogen fluoride to produce an equilibrium mixture which is an aqueous phase comprising water, bis(fluoromethyl)ether, unreacted formaldehyde and unreacted hydrogen fluoride. The presence of a solvent into which the bis(fluoromethyl)ether is preferentially extracted may allow substantially increased conversions of formaldehyde to bis(fluoromethyl)ether than would otherwise be possible, as well as simultaneously providing separation of bis(fluoromethyl)ether from water.

The formaldehyde/hydrogen fluoride aqueous phase is preferably a liquid phase, and the solvent may be in the gaseous or liquid phase, although for convenience we prefer that both the aqueous and solvent phases are liquids.

Generally the conditions of temperature and pressure under which the process is carried out will be such that the aqueous and solvent phases are both liquids. The process is conveniently effected at about ambient temperature and at about atmospheric pressure although temperatures other than ambient, say from about −20° C. to about 100° C. and subatmospheric or superatmospheric pressures, may be employed if desired.

It is to be understood that by the expression "in the presence of" is meant that the hydrogen fluoride and formaldehyde themselves and/or the reaction product mixture of contacting formaldehyde and hydrogen fluoride, are in the presence of an organic solvent for at least some time but not necessarily at all times. Thus the formaldehyde and hydrogen fluoride starting materials may be first mixed in order to form the aqueous equilibrium phase which may then be brought into contact with the solvent. Alternatively, the three components may be mixed together simultaneously and the aqueous phase may be subsequently separated from the solvent phase. In this case the three components may be mixed in any order.

Whether the formaldehyde and hydrogen fluoride are first mixed together and then brought into the presence of a solvent, or the components are mixed together simultaneously may depend at least to some extent upon the particular apparatus employed for effecting the process. For example, where the process is carried out in a series of discrete vessels, the three components may be introduced simultaneously to the first vessel and be allowed to come to equilibrium. The solvent phase comprising bis(fluoromethyl)ether and the solvent may be separated from the aqueous phase and the aqueous phase may then be transferred to a second vessel in which it is contacted with more solvent in order to extract more bis(fluoromethyl)ether from the aqueous phase, and this process may be continued through a series of vessels. Additional formaldehyde and hydrogen fluoride may be supplied to successive vessels.

For convenience and ease of operation of the process of the invention on a continuous basis however, we prefer to employ a liquid-liquid contact column or mixer-settler apparatus which allows the continuous provision of formaldehyde, hydrogen fluoride and a solvent to the column or mixer-settler apparatus and the continuous collection of an aqueous phase and a solvent phase comprising the solvent and bis(fluoromethyl)ether.

A mixer-settler apparatus comprises a series of alternating mixing and settling vessels. The aqueous and solvent phases may be introduced at opposite ends of the series of vessels and are continuously fed through the series of vessels. The phases are mixed in the mixer vessels and allowed to settle and separate in the settler vessels before being fed to the adjacent mixer vessels and the process repeated. One phase is continuously fed through the apparatus in one direction and the other phase is continuously fed through the apparatus in the opposite direction; a solvent phase is continuously collected from the aqueous phase inlet end of the apparatus and an aqueous phase is continuously collected from the solvent phase inlet end. Whilst theoretically there is no limit to the number of mixer-settler units in the series, we generally prefer to use at least 15 mixer-settler units, and more preferably at least 20 units. Liquid-liquid contact columns basically comprise a column in which there is provided means for assisting liquid-liquid contact which may be fixed or static parts, for example sieve plates or a random or ordered packing, or moving parts, for example rotating plates or grids. The column may operate with or without an energy input.

Many liquid-liquid contact columns and mixer-settler configurations and designs are known and a collection are described, for example, in Ullmann's Encyclopedia of Industrial Chemistry, Volume B3, pages 6-14 to 6-22, the contents of which are incorporated herein by reference. Any of these configurations may be employed to perform the process of the invention.

For convenience the invention will be described hereinafter with reference to the use of a liquid-liquid contact column although it is to be understood that the invention is not limited to the use of such an apparatus.

The liquid-liquid contact column, or at least the internal surfaces of the column and other components, in particular the internal components within the column, for example the packing, which are in contact with the reactant/product mixture, should be constructed from materials which are resistant to the corrosive combination of hydrogen fluoride and water. Thus, the column and associated apparatus may be constructed from, for example, a Hastelloy or Inconel alloy, or from a polyfluorinated polymer, for example polytetrafluoroethylene. The column may be made completely from such a material or the column may be constructed from, for example, steel which is then coated or lined with a material resistant to the reaction/product mixture. Under the mild conditions of temperature and pressure at which the process of the invention may be effected, the column may also be constructed from polypropylene.

The size of the column may vary considerably depending inter alia upon the desired production rate and the particular solvent employed. However, for typical commercial production rates, the number of practical stages within the column will usually be at least 10 and preferably at least 20.

There is no limit to the maximum number of stages which may be provided within the column although there is generally no need for there to be in excess of 150 stages.

We have found that it is preferable in order to balance maximum bis(fluoromethyl)ether extraction and formaldehyde conversion with the capital cost of plant construction that the column has from about 30 to about 50 practical stages.

In the embodiment of the invention in which a structured packing is employed within the column, a practical stage is measured in terms of the "height of packing equivalent to a theoretical distillation plate" or "HETP"; that is the height of packing which performs the same degree of separation as a theoretical separation stage.

The HETP depends upon the particular packing employed in the column. However, the HETP will typically be in the range from about 0.1 meter to about 1 meter. Thus the column will typically comprise from about 20 meters to about 35 meters of packing in total.

The formaldehyde and hydrogen fluoride may be fed separately to the column, or they may be pre-mixed before being introduced into the column. We generally prefer to pre-mix the formaldehyde and hydrogen fluoride as this provides a particularly convenient way of introducing formaldehyde to the column.

The formaldehyde employed in the process of the invention, either as feed to the column or which is pre-mixed with hydrogen fluoride may be provided in any of its known forms although we generally prefer to employ formaldehyde in the liquid or vapour phase. Thus the formaldehyde may be provided, for example, in one of its polymeric forms, paraformaldehyde or trioxane, or may be in the form of an aqueous solution generally known as formalin. Alternatively, the formaldehyde may be in its monomeric form, which may be provided, for example from a process stream in which it has been freshly prepared, for example by the oxidation of methanol. Accordingly, whenever used herein, the term "formaldehyde" is to be understood as including formaldehyde in any of its known forms.

We prefer to pre-mix formaldehyde and hydrogen fluoride and preferably the formaldehyde is introduced into the column in the form of a solution of formaldehyde, for example paraformaldehyde, in hydrogen fluoride, since this reduces the amount of water within the column. Also in this case some reaction will have advantageously taken place in the formaldehyde/hydrogen fluoride solution fed to the column so that the feed stream will already contain bis(fluoromethyl)ether and water.

The formaldehyde and hydrogen fluoride may be fed to the column through the same inlet, that is they may be fed to the column as a solution of formaldehyde in hydrogen fluoride. Additional hydrogen fluoride may, if desired, be introduced to the column through an additional hydrogen fluoride inlet.

The relative molar proportions of hydrogen fluoride including the hydrogen fluoride fed to the column through any additional hydrogen fluoride inlets and through the formaldehyde inlet, and formaldehyde which are introduced to the column may vary considerably, for example in the range from about 0.5:1 to about 50:1 but in general a stoichiometric excess of hydrogen fluoride is preferred. Typically the molar ratio of hydrogen fluoride to formaldehyde will be in the range from about 2:1 to about 10:1.

The particular solvent used, more than any other factor, determines the efficiency with which bis(fluoromethyl)ether is extracted from the aqueous phase in terms of both quantity and selectivity.

The solubility of bis(fluoromethyl)ether in the solvent is preferably as high as possible in order to reduce the solvent flow rate through the column and the amount of solvent required for fully extracting bis(fluoromethyl)ether from the aqueous phase, and the partition coefficient of the solvent for water is preferably as low as possible in order that as little water as possible, and preferably no water, is extracted into the solvent phase.

The solubility of bis(fluoromethyl)ether in the solvent is preferably at least 50 grammes per liter, and more preferably at least 100 grammes per liter, and more especially at least 200 grammes per liter.

The partition coefficient in the solvent of the components present in the process, namely water, formaldehyde, hydrogen fluoride and bis(fluoromethyl)ether, are respectively less than 1, preferably less than 0.5, more preferably less than 0.1 and especially less than 0.01; less than 1; less than 1; and at least 4, preferably at least 10 and especially at least 20.

Furthermore, it is preferred that the solvent is unreactive towards the aqueous equilibrium phase, as well as essentially immiscible with the aqueous equilibrium phase. We have found that certain classes of solvents, in particular many oxygen-containing solvents and lower aliphatic hydrocarbons, for example those having up to say 7 carbon atoms, are to different degrees miscible with or reactive towards the aqueous equilibrium phase, thus making them less suitable for use in the process of the invention.

The solvent is preferably one which is both immiscible with and unreactive towards the aqueous equilibrium phase. The solvent may be an inorganic solvent, for example carbon disulphide, although many suitable solvents are organic solvents and we prefer to employ an organic solvent. The organic solvent may be an optionally halogenated aliphatic (hydro)carbon which may be a straight or branched chain hydrocarbon, cyclic or acyclic. In particular, we have found that aliphatic hydrocarbons having or more carbon atoms, for example iso-octane but especially aliphatic halocarbons having one or more carbon atoms, which preferably contain at least one atom of chlorine or fluorine but especially at least one atom of chlorine, have provided selective extraction of bis(fluoromethyl)ether without reaction or miscibility with the aqueous equilibrium phase.

The organic solvent is preferably a chlorohydrocarbon having from 1 to 6 carbon atoms, for example chloroform or 1,1-dichloroethane, a hydrochlorofluorocarbon having from 1 to 6 carbon atoms, for example dichloromonofluoroethane or dichlorotrifluoroethane, or a perhalogenated alkane, for example trichlorotrifluoroethane.

Mixtures of solvents may be employed if desired.

In a preferred embodiment of the invention, the formaldehyde and hydrogen fluoride are pre-mixed and introduced into the column at one end and the solvent is introduced at the other end of the column in order that the aqueous and solvent phases flow in counter-current to each other through the column.

The direction of flow of the aqueous and solvent phases through the column depend upon the relative densities of the two phases and the solvent may be more or less dense than water and thus the solvent may be fed to the top or bottom of the column and the aqueous phase fed to the bottom or top of the column respectively as required.

The efficiency of phase separation during the extraction is dependent upon the density difference between the solvent and aqueous hydrogen fluoride. The solvent preferably has a density difference, with respect to aqueous hydrogen fluoride, of at least 50 kg/m$^3$, more preferably at least 70 kg/m$^3$ and especially at least 100 kg/m$^3$.

The flow rates of the aqueous and solvent phases through the column are such as to maximise the extraction of bis(fluoromethyl)ether from the aqueous phase, although, the flow rates will be dependent to some extent on the size of the column and the absolute and relative proportions of aqueous and solvent phases as well as the conditions under which the column is operated.

The solvent phase which is withdrawn from the column comprises a solution of bis(fluoromethyl)ether in the solvent. Preferably, the solvent is one which is easily separable from the bis(fluoromethyl)ether, by conventional means, for example distillation. Thus, the solvent preferably has a different boiling point to that of bis(fluoromethyl)ether, usually a higher boiling point than that of bis(fluoromethyl)ether. Preferably the solvent and bis(fluoromethyl) ether have a difference in boiling point of at least 50° C.

The process of the invention facilitates production of bis(fluoromethyl)ether of sufficiently high purity (relative to water) that the bis(fluoromethyl)ether stream may be fed, optionally after removing the solvent from the ether, to a reaction zone in which the bis(fluoromethyl)ether is converted to difluoromethane.

According to a further aspect of the invention there is provided a process for the production of difluoromethane which comprises (a) producing bis(fluoromethyl)ether by contacting formaldehyde with hydrogen fluoride in the presence of an essentially water-immiscible solvent for the ether and (b) feeding the bis(fluoromethyl)ether to a reaction zone whereby to convert the bis(fluoromethyl)ether to difluoromethane.

The bis(fluoromethyl)ether/solvent mixture from step (a) may be passed directly to step (b). Preferably, however, the bis(fluoromethyl)ether is separated from the solvent prior to step (b) of the process.

Step (b) of this preferred embodiment of the invention may be effected in the liquid or vapour phase. We prefer that step (b) is effected in the vapour phase by heating the bis(fluoromethyl)ether from step (a) to elevated temperature, preferably in the presence of a suitable catalyst. Preferably therefore the bis(fluoromethyl)ether from step (a) is fed to a heating zone preferably containing a catalyst.

This preferred manner of effecting step (b) of the process is described in European Patent Application No. 91 12817.3, Publication No. 0 518 506, the contents of which are incorporated herein by reference.

Heating of the bis(fluoromethyl)ether may be carried out in the presence of hydrogen fluoride vapour.

Heating of the bis(fluoromethyl)ether in step (b) to produce difluoromethane may advantageously be performed in the presence of a catalyst. The conversion of bis(fluoromethyl)ether and selectivity to difluoromethane are dependent upon the choice of catalyst and we have found that whilst certain catalysts promote a high degree of selectivity to difluoromethane, other catalysts promote a high degree of selectivity to monofluoromethane and still other catalysts yield mixtures of both difluoromethane and monofluoromethane.

The catalyst may be for example a metal, including for example an s-block metal such as calcium, a p-block metal such as aluminium, tin or antimony, an f-block metal such as lanthanum or a d-block metal such as nickel, copper, iron, manganese, cobalt and chromium or alloys thereof; a metal oxide, for example chromia or alumina, a metal fluoride, for example, aluminium, manganese or chromium fluoride, or a metal oxyfluoride, for example an oxyfluoride of one of the aforementioned metals. The metal is preferably a d- or p- block metal, oxide, fluoride or oxyfluoride thereof, and more preferably is chromium, aluminium, or a Group VIIIa metal.

We have found that difluoromethane may be produced in step (b) with very high selectivity where the catalyst employed is a metal selected from the group consisting of nickel, aluminium, iron or chromium and in particular where the catalyst is an alloy or mixture of at least one of these metals. The alloy or mixture may also comprise other metals, for example molybdenum, copper or cobalt. Examples of preferred alloys include Hastelloy and stainless steel; stainless steel is an especially preferred alloy.

Furthermore we prefer that the catalyst is treated with air (or oxygen) prior to use, that is the catalyst is heated to elevated temperature in the presence of air, for example a temperature in the range from 300° C. to 500° C. Alternatively or additionally this catalyst pre-treatment may be carried out in the presence of hydrogen fluoride.

Further preferred catalysts are chromia and iron oxide, which although they may not promote as high a degree of selectivity to difluoromethane as the preferred alloys, are very robust catalysts. Chromia and iron oxide may also be given a pre-treatment prior to their use.

The catalyst may also comprise mixtures of metals, oxides, fluorides or oxyfluorides thereof, such as for example impregnated metal oxide or oxyfluorides, or simple mixtures. Thus, for example the catalyst may comprise chromia impregnated with iron, nickel, copper or other metals or compounds thereof, for example oxides or halides thereof or the catalyst may comprise a mixture of chromia and other metal oxides, for example iron oxide.

Other catalysts may also be used which lead to the production of monofluoromethane with a high degree of selectivity, for example a catalyst comprising zinc impregnated chromia or tin fluoride.

The catalyst may be supported or unsupported.

Accordingly in a further preferred embodiment of the invention, step (b) comprises heating bis(fluoromethyl)ether in the vapour phase at elevated temperature in the presence of a catalyst and optionally also in the presence of hydrogen fluoride. The catalyst is preferably at least one metal, metal oxide, metal fluoride or metal oxyfluoride.

According to a still further preferred embodiment of the invention, step (b) comprises heating bis(fluoromethyl)ether in the vapour phase at elevated temperature in the presence of a catalyst comprising a metal selected from the group consisting of nickel, chromium, aluminium and iron or an alloy of at least one of these metals or an oxide, fluoride or oxyfluoride thereof.

The temperature to which the bis(fluoromethyl)ether is heated in step (b) is dependant at least to some extent on whether the heating is effected in the presence of a catalyst. Where the heating is effected in the presence of a catalyst the preferred temperature is dependent on the particular catalyst used; generally where a catalyst is present the temperature need not be as high as when a catalyst is not present.

Typically the temperature need be no higher than about 450° C. where a catalyst is used in the presence of hydrogen fluoride. Thus, for example, where the heating is effected in the presence of stainless steel and hydrogen fluoride, the temperature is preferably at least about 250° C. and more preferably at least 300° C. but need be no higher than about 400° C., generally no higher than about 350° C. However, where the catalyst is chromia in the presence of hydrogen fluoride, the temperature is preferably from about 180° C. to about 320° C., more preferably from about 200° C. to about 280° C.

Step (b) of the process is conveniently carried out at about ambient pressure although superatmospheric or subatmospheric pressures may be used if desired. Indeed superatmospheric pressures up to about 15 bar at lower temperatures may be generally preferred since the yield of and selectivity to difluoromethane may be increased under such conditions.

After completion of step (b), the difluoromethane may be isolated from unchanged starting materials and by-products using conventional procedures, for example distillation.

Figure 2:
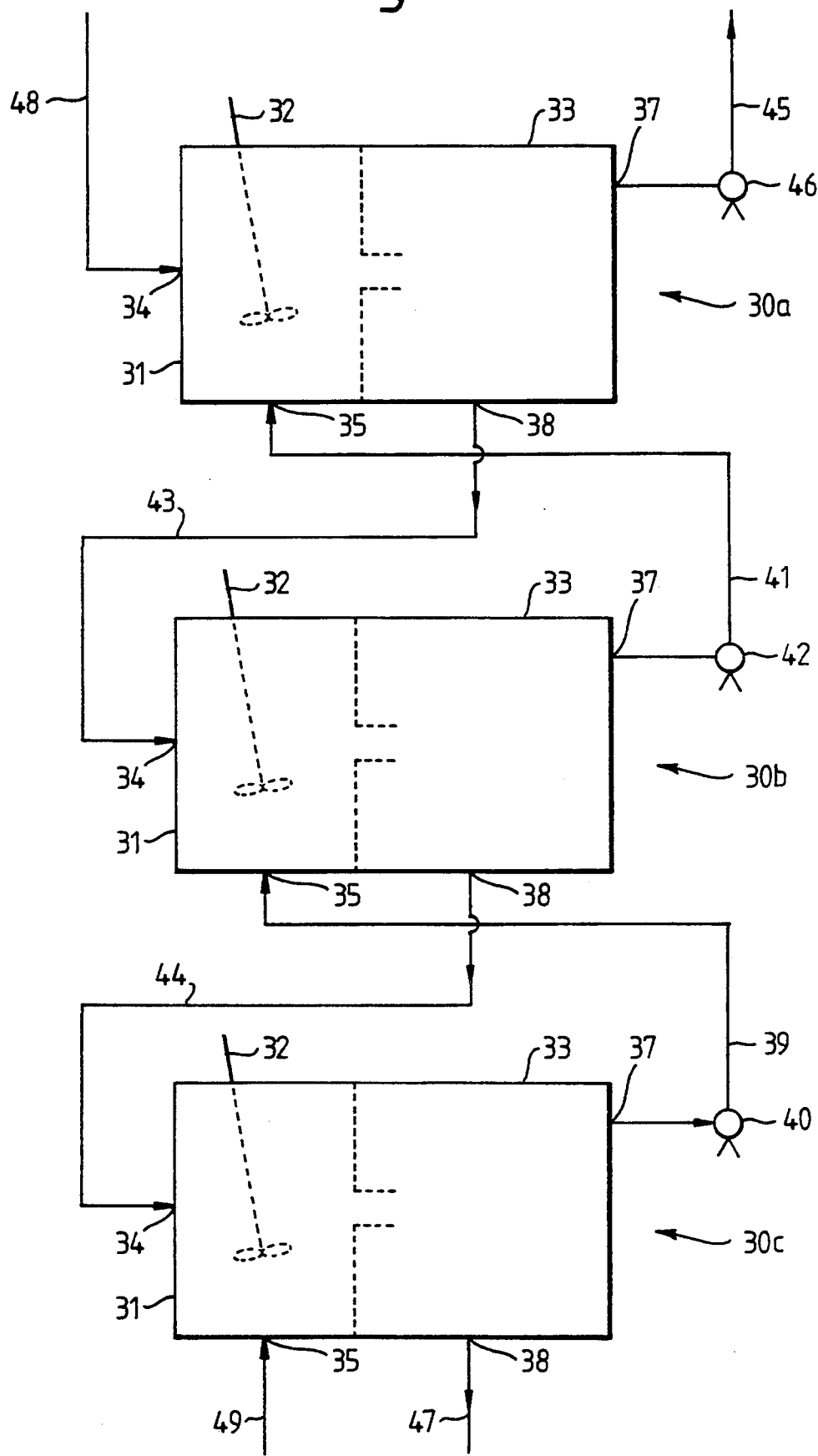

Two preferred embodiments of the invention are illustrated with reference to the drawings in which:

FIG. 1 is a schematic flow diagram illustrating operation of the process of the invention in a packed column, and FIG. 2 is a schematic flow diagram illustrating operation of the process of the invention in a mixer-settler apparatus.

In the apparatus shown in FIG. 1, a packed column 1, has a hydrogen fluoride/formaldehyde inlet 2, a hydrogen fluoride/water outlet 3, a solvent inlet 4, a bis(fluoromethyl)ether/solvent outlet 5 and a hydrogen fluoride recycle inlet 6. The column is packed with packing 7. The column and the packing may be made of Inconel alloy.

In using the apparatus, hydrogen fluoride and formaldehyde are fed to the inlet 2 through line 8 from a pre-mixer vessel 9 provided with an inlet 10 for formaldehyde and an inlet 11 for hydrogen fluoride. The pre-mixer vessel is provided with a planetary stirrer 12.

The apparatus further comprises a distillation column 13 to which bis(fluoromethyl)ether and solvent (hereafter referred to as the organic phase) are fed from outlet 5 of the column through line 14 and inlet 15. Solvent collected from the bottom of column 13 is fed through line 16 to the solvent inlet 4 to column 1.

Water and hydrogen fluoride from outlet 3 of column 1 are fed through line 17 to a distillation column 18. The distillation column 18 is connected via a hydrogen fluoride outlet 19 and through line 20 to hydrogen fluoride recycle inlet 6.

In operation of the column 1, formaldehyde and hydrogen fluoride are fed to the pre-mixer vessel 9 where they are mixed by the stirrer 12, and then through line 8 and inlet 2 to the top of the column 1. Formaldehyde and hydrogen fluoride react on mixing to form bis(fluoromethyl)ether and water, and this aqueous phase, which is more dense than the organic solvent, flows downwardly through the column.

The solvent is fed to the bottom of the column 1 and whilst flowing upwardly through the column in counter-current to the aqueous phase, bis(fluoromethyl)ether is preferentially extracted from the aqueous phase into the solvent.

The aqueous phase leaves the bottom of the column and is fed to the distillation column 18, where water is separated from hydrogen fluoride using sulphuric acid. The hydrogen fluoride is recycled via line 20 to the column 1 through inlet 6.

The organic phase leaves the top of the column via outlet 5 and line 14 and is fed to the distillation column 13, where the solvent is separated from bis(fluoromethyl)ether. The bis(fluoromethyl)ether is collected from the top of column 13, whilst the organic solvent is returned to the column 1 via inlet 4.

FIG. 2 shows an alternative apparatus in which column 1 in FIG. 1 is replaced by a mixer-settler apparatus 30. In the apparatus of FIG. 2, three mixer-settler units only are shown for clarity although in practice, many more such units may be connected in series.

The apparatus in FIG. 2 comprises three mixer settler units; two end units 30a, and 30c and a central unit 30b, each unit comprising a mixing chamber 31, provided with a planetary stirrer 32, and a settler chamber 33. The mixer chamber 31 is provided with an aqueous phase inlet 34 (formaldehyde/hydrogen fluoride in respect of unit 30a), and an organic phase inlet 35 (organic solvent in respect of unit 30c). The settler chamber 33 is provided with an organic phase outlet 37 and an aqueous phase outlet 38.

The organic phase outlet 37 from settler chamber 33 of unit 30c is connected through line 39 and pump 40 to organic phase inlet 35 of the mixer chamber 31 of the adjacent unit 30b, and the organic phase outlet 37 of settler chamber 33 of unit 30b is connected through line 41 and pump 42 to the organic phase inlet 35 of mixer chamber 31 of the adjacent unit 30a. The aqueous phase outlet 38 from settler chamber 33 of unit 30a is connected through line 43 to inlet 34 of the mixer chamber 31 of the adjacent unit 30b and the aqueous outlet 38 from the settler chamber 33 of unit 30b is connected through line 44 to inlet 34 of mixer chamber 31 of the adjacent unit 30c.

The organic phase outlet 37 of settler chamber 33 of unit 30a is connected through line 45 and pump 46 to a distillation column (not shown but equivalent to 13 in FIG. 1) in which the organic solvent is separated from bis(fluoromethyl)ether. The aqueous phase outlet 38 of settler chamber 33 of unit 30c is connected through line 47 to a distillation column (not shown but equivalent to 18 in FIG. 1) in which water is separated from the hydrogen fluoride.

In operation of the apparatus, an aqueous feed stream comprising hydrogen fluoride and formaldehyde is fed from a pre-mixer (not shown but equivalent to 9 in FIG. 1) to mixer chamber 31 of unit 30a through line 48, and organic solvent is fed to mixer chamber 31 of unit 30c through line 49. The aqueous phase is stirred in mixer chamber 31 of unit 30a with the organic phase fed via line 41 from unit 30b and fed to the settler chamber 33 where an aqueous phase separates out from an organic phase. The aqueous phase is fed through line 43 to mixer chamber 31 of unit 30b and the organic phase is fed through line 45 and pump 46 to the distillation column 13. The organic phase is stirred in mixer chamber 31 of unit 30c with the aqueous phase fed via line 44 from unit 30b and fed to settler chamber 33 where an aqueous phase separates from an organic phase. The organic phase is fed through line 39 and pump 40 to mixer chamber 31 of unit 30b and the aqueous phase is fed through line 47 to column 18.

In mixer chamber 31 of unit 30b, the aqueous phase from settler chamber 33 of unit 30a and the organic phase from settler chamber 33 of unit 30c are mixed and the resulting dispersion is fed to settler chamber 33 of unit 30b where aqueous and organic phases are allowed to separate out. The organic phase is then fed to the mixer chamber 31 of unit 30a through line 41 and pump 42 and the aqueous phase is fed to mixer chamber 31 of unit 30c through line 44. In this manner the aqueous and organic phases are fed through the apparatus in counter-current manner, the organic and aqueous phases being mixed and then allowed to separate in the respective chambers of each unit.

In practice, the apparatus comprises many mixer/settler units, with the process described in central unit 30b, being repeated in each unit. As is described for the apparatus shown in FIG. 1 the solvent may, after separation from bis(fluoromethyl)ether in distillation column 13, be recycled through line 49 to the apparatus, and hydrogen fluoride may, after separation from water in distillation column 18, be recycled to the apparatus.

The invention is illustrated but not limited by the following examples.

EXAMPLE 1 AND COMPARATIVE EXAMPLE

In this example, a variety of solvents were subjected to the qualitative procedure outlined below: 9 g of trioxane was added to 30 g of anhydrous hydrogen fluoride and to this mixture was added 10 ml of the chosen solvent. The mixture was observed. The resulting observations for the chosen solvents are detailed below:

| SOLVENT: | OBSERVATION. |
| --- | --- |
| Diethyl ether | Miscible |
| Butyl ethyl ether | Miscible |
| Iso-propyl ether | Miscible |
| Ethyl acetate | Miscible |
| Cyclohexanone | Hiscible |
| methyl isobutyl ketone | Miscible |
| Cyclohexane | Reaction |
| n-hexane | Reaction |
| Toluene | Reaction |
| Perfluorodecalin | Immiscible-no reaction |
| Trichlorotrifluoroethane | Immiscible-no reaction |
| Carbon tetrachloride | Immiscible-no reaction |
| Carbon disulphide | Immiscible-no reaction |
| Dichlorotrifluoroethane | Immiscible-no reaction |
| Dichlorofluoroethane | Immiscible-no reaction |
| Iso-octane | Immiscible-no reaction |
| Chloroform | Immiscible-no reaction |
| Trichloroethylene | Immiscible-no reaction |
| Dichloromethane | Immiscible-no reaction |
| 1,2-dichloroethane | Immiscible-no reaction |

EXAMPLE 2

In this example, five of the solvents which were found to be immiscible and unreactive towards the formaldehyde/hydrogen fluoride product mixture were subjected to the following quantitative general procedure in order to determine their preferential extraction of bis(fluoromethyl)ether.

9 g of trioxane were added to 30 g of anhydrous hydrogen fluoride to give a 5:1 molar ratio of hydrogen fluoride to formaldehyde. 10 ml of the chosen solvent were then added to this mixture and the solvent decanted. Two further 10 ml aliquots of solvent were added and decanted from the formaldehyde/hydrogen fluoride product mixture. The solvent extracts were then combined together and analysed for their bis(fluoromethyl)ether and water contents by Gas Chromatography using a Thermal Conductivity Detector. The results are shown in Table 1.

TABLE 1

| SOLVENT | BFME moles | $H_2O$ moles |
| --- | --- | --- |
| 1,2-dichloroethane | 0.022 | N.D. |
| Chloroform | 0.016 | <0.002 |
| Iso-octane | 0.002 | N.D. |
| Dichlorotrifluoroethane | 0.023 | <0.002 |
| Dichlorofluoroethane | 0.008 | <0.001 |

EXAMPLE 3

The procedure of example 2 was repeated except that the solvents employed were chloroform and 1,2-dichloroethane, and the formaldehyde/hydrogen fluoride mixture was analysed prior to adding the first aliquot of solvent and after the third aliquot had been separated from it, for its bis(fluoromethyl)ether, water and formaldehyde content. The results are shown in Table 2.

TABLE 2

| SOLVENT. | BFME (moles) | $CH_2O$ (moles) | $H_2O$ (moles) |
|---|---|---|---|
| (A) CHLOROFORM. | | | |
| $CH_2O$/HF Mixture before $CHCl_3$ added. | 0.0902 | 0.2079 | 1.334 |
| $CH_2O$/HF Mixture after $CHCl_3$ extraction. | 0.0744 | 0.1428 | 1.454 |
| $CHCl_3$ extract. | 0.0221 | N.D. | 0.0029 |
| (B) 1,2-DICHLOROETHANE. | | | |
| $CH_2O$/HF Mixture before $C_2H_4Cl_2$ added. | 0.0902 | 0.2079 | 1.334 |
| $CH_2O$/HF Mixture after $C_2H_4Cl_2$ extraction. | 0.0642 | 0.1233 | 1.079 |
| $C_2H_4Cl_2$ extract. | 0.0257 | 0.0026 | N.D. |

The following examples 4 to 7 illustrate step (b) of the further aspect of the invention.

EXAMPLE 3

Heating BFME in the Presence of HF-Treated Chromia

Bis(fluoromethyl)ether was vaporised by bubbling nitrogen through liquid bis(fluoromethyl)ether at room temperature at a flow rate of 75 mls/minute. The vapour was fed to an Inconel tube (length 12 inches and diameter 1 inch) packed with 120 g of chromia pellets which had been pre-treated by heating the pellets to 350° C. for 4 hours in a stream of hydrogen fluoride having a flow rate of 150 ml/minute. The tube was heated from room temperature to elevated temperature and the composition of the reactor off gas was followed (Gas Chromatography) as a function of temperature and the results are shown in Table 3.

TABLE 3

| Temp/°C. | % Yield | | BFME Conversion/% | Molar Ratio $CH_2F_2/CH_3F$ |
|---|---|---|---|---|
| | $CH_3F$ | $CH_2F_2$ | | |
| 185 | 29.11 | 43.79 | 74.38 | 1.5 |
| 224 | 32.34 | 62.54 | 95.71 | 1.93 |
| 246 | 35.40 | 63.77 | 99.97 | 1.8 |
| 256 | 35.22 | 62.21 | 100.0 | 1.77 |
| 292 | 35.66 | 57.45 | 98.09 | 1.61 |
| 320 | 35.88 | 54.57 | 97.62 | 1.52 |

EXAMPLE 4

Heating BFME in the Presence of Nickel Doped Chromia 100 g of chromia pellets were added to a saturated aqueous solution of nickel nitrate and the water was then removed by direct heating to 150° C., to give a 2.7% nickel impregnated chromia catalyst. 100 g of the catalyst was charged to an Inconel reactor (length 12 inches and diameter 1 inch) and heated in nitrogen at 300° C. for 28 hours and then pre-fluorinated by heating in hydrogen fluoride at 350° C. for 4 hours. Finally the catalyst was heated in nitrogen at 250° C. for 15 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 4.

TABLE 4

| Temp/°C. | % Yield | | BFME Conversion/% | Molar Ratio $CH_2F_2/CH_3F$ |
|---|---|---|---|---|
| | $CH_3F$ | $CH_2F_2$ | | |
| 223 | 36.78 | 60.35 | 97.14 | 1.64 |
| 234 | 28.25 | 69.10 | 97.35 | 2.45 |
| 241 | 21.60 | 77.56 | 99.16 | 3.6 |
| 251 | 23.42 | 73.27 | 97.82 | 3.13 |
| 265 | 26.48 | 71.64 | 98.12 | 2.7 |
| 279 | 24.45 | 72.35 | 99.53 | 3.0 |

EXAMPLE 5

Heating BFME in the Presence of Mixed Iron OXIDE/CHROMIA 112.7 g of a catalyst comprising 9:1 by weight iron (III) oxide and chromia was charged to an Inconel reactor (length 12 inches and diameter 1 inch) and heated in hydrogen fluoride at 300° C. for 12 hours. The catalyst was then heated in nitrogen at 230° C. for 15 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 5.

TABLE 5

| Temp/°C. | % Yield | | BFME Conversion/% | Molar Ratio $CH_2F_2/CH_3F$ |
|---|---|---|---|---|
| | $CH_3F$ | $CH_2F_2$ | | |
| 223 | 23.34 | 73.52 | 99.15 | 3.15 |
| 235 | 19.33 | 68.41 | 87.75 | 3.54 |

EXAMPLE 6

Heating BFME in the Presence of Pre-Fluorinated Aluminium Fluoride 103.9 g of aluminium fluoride was charged to an Inconel reactor (length 12 inches and diameter 1 inch), heated in nitrogen at 300° C. for 4 hours and then heated in hydrogen fluoride at 300° C. for 12 hours. The catalyst was then heated in nitrogen at 240° C. for 16 hours.

Bis(fluoromethyl)ether was vaporised by bubbling nitrogen through liquid bis(fluoromethyl)ether at room temperature at a flow rate of 75 mls/minute. The vapour was fed to the Inconel reactor. The tube was heated from room temperature to elevated temperature and the composition of the reactor off gas was followed (Gas Chromatography) as a function of temperature and the results are shown in Table 6.

TABLE 6

| Temp/°C. | % Yield | | BFME Conversion/% | Molar Ratio $CH_2F_2/CH_3F$ |
|---|---|---|---|---|
| | $CH_3F$ | $CH_2F_2$ | | |
| 235 | 30.46 | 68.5 | 98.96 | 2.25 |

We claim:
1. A process for the production of bis(fluoromethyl)ether which comprises contacting formaldehyde with hydrogen fluoride to produce an aqueous phase comprising water and bis(fluoromethyl)ether wherein the contact is effected in the presence of a solvent for the ether which is essentially water-immiscible and unreactive towards the aqueous phase whereby said ether is preferentially extracted into said solvent.

2. A process as claimed in claim 1 which comprises separating a solvent phase comprising less than an equimolar amount of water relative to bis(fluoromethyl)ether from an aqueous phase.

3. A process as claimed in claim 1 which comprises (a) contacting formaldehyde with hydrogen fluoride and (b) contacting the product of step (a) with the solvent.

4. A process as claimed in any one of claims 1 to 3 in which the formaldehyde is contacted with hydrogen fluoride in the liquid phase.

5. A process as claimed claim 4 in which the solvent is in the liquid phase.

6. A process as claimed in any one of claims 1 to 3 in which the process is effected in a mixer-settler apparatus.

7. A process as claimed in any one of claims 1 to 3 in which the process is effected in a liquid-liquid contact column.

8. A process as claimed in claim 3 in which in step (b) the product of step (a) is caused to flow in counter-current to the solvent.

9. A process as claimed in any one of claims 1 to 3 in which the solvent comprises an optionally halogenated aliphatic (hydro)carbon.

10. A process as claimed in any one of claims 1 to 3 in which the solvent comprises a chlorocarbon.

11. A process as claimed in any one of claims 1 to 3 in which the solvent comprises a chlorine-containing alkane having from 1 to 4 carbon atoms.

12. A process for the production of difluoromethane which comprises the steps of (a) producing bis(fluoromethyl)ether by contacting formaldehyde with hydrogen fluoride in the presence of an essentially water-immiscible solvent for the ether as defined in any one of claims 1 to 3 and (b) feeding the bis(fluoromethyl)ether to a reaction zone and heating the bis(fluoromethyl)ether to elevated temperature in the vapour phase in the presence of a catalyst to convert the bis(fluoromethyl)ether to difluoromethane.

13. A process as claimed in claim 12 which comprises the step of separating the ether from the solvent and feeding bis(fluoromethyl)ether to step (b).

14. A process as claimed in claim 12 in which the catalyst comprises a metal selected from the group consisting of nickel, chromium, aluminium and iron or an alloy of at least one of these metals, or an oxide, fluoride or oxyfluoride thereof.

15. A process according to claim 1 which comprises premixing formaldehyde with hydrogen fluoride to form an aqueous phase comprising water, bis(fluoromethyl)ether, unreacted hydrogen fluoride and unreacted formaldehyde and contacting this aqueous phase with a solvent for the ether which is essentially water-immiscible and unreactive towards the aqueous phase, said solvent being a chlorohydrocarbon containing 1–6 carbon atoms, said aqueous phase and solvent being in contact through counter-current flow thereof said ether is preferentially extracted from the aqueous phase into said solvent.

* * * * *